ial. ........................ 128/681

United States Patent [19]

Richley et al.

[11] Patent Number: 5,025,793
[45] Date of Patent: Jun. 25, 1991

[54] FINGER BLOOD PRESSURE MEASUREMENT SYSTEM

[76] Inventors: Edward A. Richley, 1929 Crisanto, #226, Mountain View, Calif. 94040; Christopher E. Russell, 348 Central Dr., Mars, Penn. 16046

[21] Appl. No.: 250,989

[22] Filed: Sep. 29, 1988

Related U.S. Application Data

[63] Continuation of Ser. No. 916,229, Oct. 7, 1986, abandoned.

[51] Int. Cl.⁵ .............................................. A61B 5/022
[52] U.S. Cl. ..................................... 128/677; 128/678
[58] Field of Search .............................. 128/677–678, 128/680–683, 687

[56] References Cited

U.S. PATENT DOCUMENTS

| 2,452,799 | 11/1948 | Speaker et al. ............... 128/687 |
| 3,149,628 | 9/1964 | Bolie ........................... 128/680 |
| 3,536,062 | 10/1970 | Horn ............................ 128/683 |
| 3,811,439 | 5/1974 | Brown .......................... 128/681 |
| 3,903,872 | 9/1975 | Link ............................. 128/ |
| 3,905,353 | 9/1975 | Lichowsky .................... 128/677 |
| 4,009,709 | 3/1977 | Link et al. .................... 128/ |
| 4,074,711 | 2/1978 | Link et al. .................... 128/ |
| 4,106,498 | 8/1978 | Haney .......................... 128/681 |
| 4,154,238 | 5/1979 | Link ............................. 128/ |
| 4,174,707 | 11/1979 | Link ............................. 128/ |
| 4,206,764 | 6/1980 | Williams ....................... 128/677 |
| 4,263,918 | 4/1981 | Swearingen et al. ........... 128/681 |
| 4,427,013 | 1/1984 | Nunn ........................... 128/ |
| 4,437,470 | 3/1984 | Prost ............................ 128/ |
| 4,469,107 | 9/1984 | Asmar et al. ................. 128/681 |

Primary Examiner—William E. Kamm
Assistant Examiner—John D. Zele

[57] ABSTRACT

A system for blood pressure measurement ascertains blood pressure indirectly by the oscillometric method at the user's index finger. Finger measurement allows the system to be smaller and easier to use than systems using conventional upper arm measurement. By using the oscillometric technique, the system according to the invention needs no microphone and so avoids the problems associated with microphone positioning. The system employs a rigid finger cuff with an inflatable inner bladder. The system extracts pulse signals transmitted via air pressure while simultaneously providing accurate pressure control.

14 Claims, 3 Drawing Sheets

FINGER BLOOD PRESSURE MEASUREMENT SYSTEM

This application is a continuation of application Ser. No. 916,229, filed Oct. 7, 1986 now abandoned.

The invention relates to a system for automatic indirect measurement of blood pressure in a human finger.

A well-known blood pressure measurement method is the auscultatory method. The auscultatory method is the familiar "doctor's office" method by which a cuff is inflated on the upper arm and a stethoscope is positioned over the patient's artery just below the cuff. After the cuff is inflated, it is slowly deflated while the doctor listens for pulsations in the artery. The cuff pressure at which pulsations begin is taken as the systolic pressure. At a lower pressure, these pulsations disappear. This pressure is taken as the diastolic pressure. Many automated blood pressure measurement devices follow this auscultatory method. Instead of a stethoscope, they use a microphone to detect the pulsations. This allows the use of electronic circuitry to determine systolic and diastolic pressures.

A drawback to the auscultatory method is that the pulsations in the artery are not always easy to detect. The readings depend strongly on microphone positioning and artery location.

After the auscultatory method was developed, it was determined that pulsations could be detected in the air of the cuff itself. A method based on this phenomena is known as the oscillometric method. The oscillometric method avoids the noted drawback of the auscultatory method because it does not employ to microphone. The entire cuff collects the pulse sounds and so alleviates the problem of positioning a microphone. The system according to the invention employs the oscillometric method and so has no microphone. The device employed by the system according to the invention which is used to measure cuff pressure is also used to detect the blood pulsations. The cuff pressure signal and blood pulsation signal are separated electronically and fed to a computer.

Blood pressure measurement taken on the upper arm is the most common method used by doctors and by some automated machines. Recent research has known that blood pressure measurements can be taken on fingers and will generally show very good agreement with upper arm measurements. The convenience of such finger measurements is a feature of the system according to the invention. Furthermore, a system according to the invention employs a combination of sensitive measurement electronics and a computer, such as a microprocessor, to determine blood pressure. The operation consists of a "measurement" phase and an "analysis" phase. Both of these phases are controlled by the system's microprocessor.

The invention may be better understood from a reading of the following detailed description in conjuction with the drawings in which.

There are practical problems associated with implementing indirect finger blood pressure measurements. Primarily these problems are due to the small size of fingers and the small amount of blood flow as compared to upper arm schemes.

A noted previously, blood pressure measurement is conventionally done by inflating a cuff around a limb so as to occlude arteries. Pressure in the occluding cuff is varied (typically it is bled down) while blood flow is detected. Analysis of these flow measurements with respect to the pressure measurement results in values for systolic, diastolic, and, possibly, means pressures. Flow may be detected by any of several means. The two most common ways are with a microphone (auscultatory) and from slight, fast variations in cuff pressure (oscillimetric). A system according to the invention employs the oscillometric technique, although much of the technique would be applicable to other methods as well.

Figure 1:
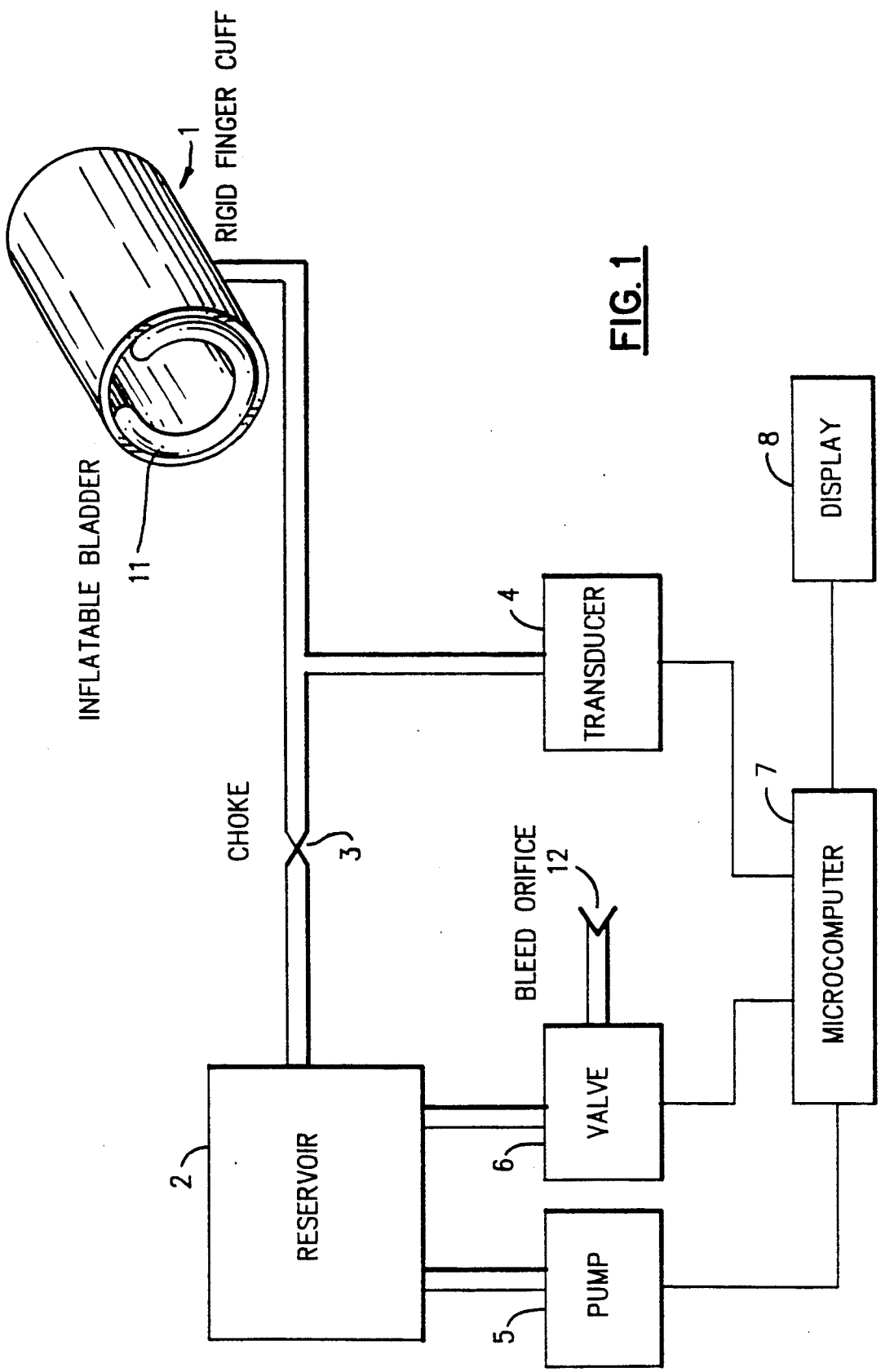
FIG. 1 shows a block diagram of a system according to the invention.
Figure 2:
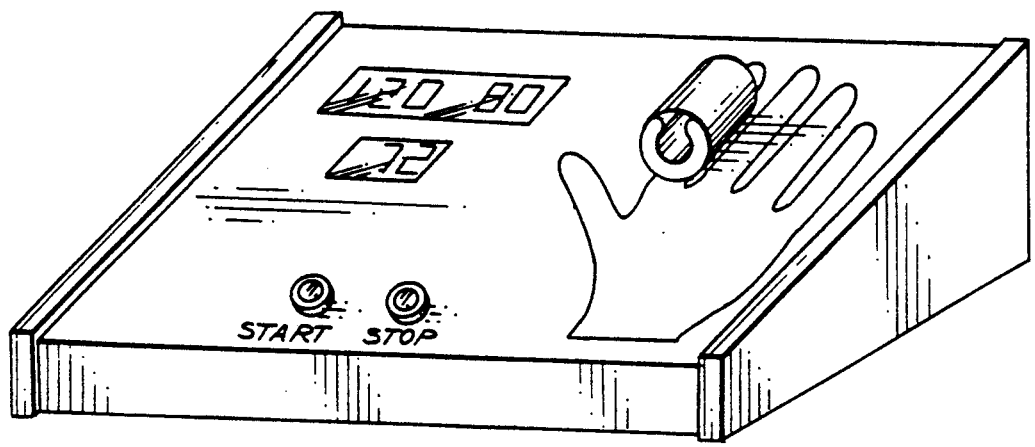
FIG. 2 shows an embodiment of the invention wherein a finger blood pressure measurement cuff is machine-mounted.
Figure 3:
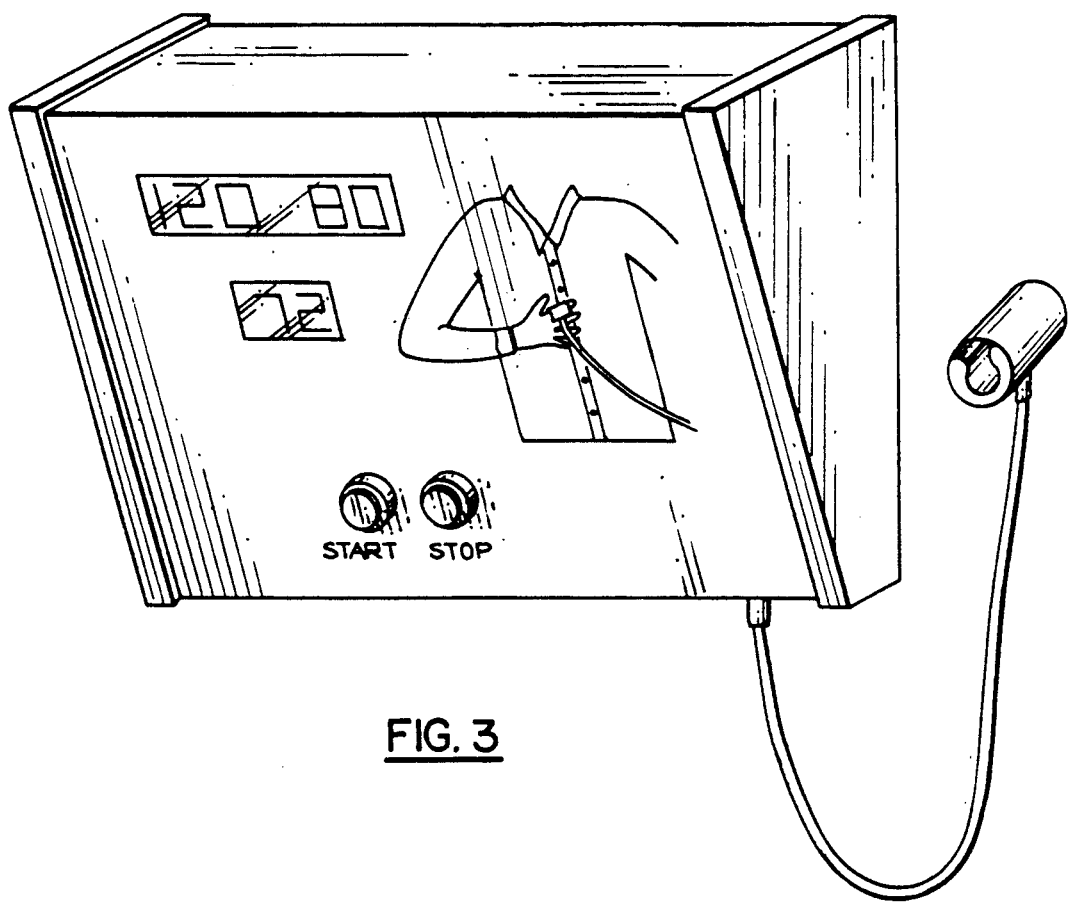
FIG. 3 shows an alternative embodiment of the invention wherein a finger blood pressure measurement cuff is adapted for practical machine-remote employment.

FIG. 1 shows a block diagram of the system. The small scale of finger measurements requires the use of a small cuff. A small, rigid, plastic tube 1 is fitted with an inflatable cloth covered bladder 11. This bladder serves to occlude finger arteries when pressure is applied. However, accurate control of pressure in such a small bladder is difficult with readily available pumps and valves. Small leaks become very important with such a low air volume. The slow response time of electric valves make accurate pressure bleed impossible. Pressure plusations caused by reciprocating pumps are not adequately filtered by such a small cuff, making accurate pressure measurement during pump-up impossible.

In order to overcome the difficulties caused by the low air volume present in the finger cuff, an air pressure reservoir 2 is employed. This serves to increase the air volume to a point where accurate pressure control during both pumping and bleeding can be obtained.

The lack of a significant amount of blood flow in human fingers makes the problem of blood flow detection difficult. In order to use the oscillometric technique, small presssure variations induced on the cuff pressure must be detected. For this method, a cuff volume as small as possible is desired so that the greatest possible pressure change will result, from the blood flow. This requirement is in direct contradiction with the desire for a larger air volume mentioned in the preceding paragraph. If the system volume is too large, pulses are "swallowed up" by the reservoir. However, in a system according to the invention, by connecting the cuff to the reservoir via a small orifice, or "choke" 3, the advantages of the reservoir volume for pressure control can be maintained while "pulse" signals are effectively isolated to the cuff side of the system. Thus, the choke serves as a filter . Pressure transducer 4 is connected at its input to a point between the choke and the cuff and as its output to microcomputer 7. Presssure transducer 4 can be a semiconductor pressure transducer as disclosed in an article entitled "Designing with Semiconductor Pressure Sensors" by R. Frank which appeared in Machine Design, Nov. 21, 1985, pp. 103–107. Slow system pressure changes are transmitted to the cuff with a slight delay, while the faster pressure pulses due to blood flow are concentrated in the cuff side where the pressure measurement device is located. The transducer signal is then split into A.C. and D.C. components (as with any oscillometric system) for measurement of pulses and cuff pressure, respectively. The microcomputer 7 then controls the pump-up of pump 5, bleed-down through valve 6 and bleed orifice 12, pulse and pressure measuremnt and interpretation. Measurement results for heart rate, systolic pressure, and diastolic pressure are then displayed to the user via play 8. At the same time, the cuff will deflate and the user can remove his or her finger. At no point during the operation will the cuff pressure reach a dangerous level. Should the user wish to abort the measurement, a stop button can be operated to allow the cuff to deflate. Even at full pressure, the user can easily remove his or her finger by pulling the finger back and out of the cuff.

The measurement phase of operation consists of collecting the pulsation information at a series of cuff pressures. The pressure is brought down in steps of approximately 8 mmHg by the action of a small valve which is controlled by the computer. At each step, the computer "listens" for blood pulsations. To avoid mistaking a random movement or sound for a blood pulsation, the computer requires there to be two similar pulse sounds at each step before the data is accepted. Of course, if there is no pulse sound in a reasonable amount of time the system proceeds to the next step. This process continues until the cuff pressure is below the lowest pressure expected for diastolic pressure in adults.

The determination of systolic and diastolic pressures from the pulse information of the oscillometric method is very different from that of the auscultatory method. Basically, a pressure at which plusations are increasing as pressure is stepped down is taken as the systolic pressure. Likewise, a pressure at which pulsations begin to decrease is taken as diastolic pressure. Thus, the measurement of blood pressure via the oscillometric method focuses on determining changes in the strength of pulsations. This is in contrast with the auscultatory method which looks for the absolute appearance and disappearance of pulsations.

This interpretation of the pulsation information occurs during the analysis phase of operation. The analysis phase occurs very quickly at the end of the test. However, it is very important phase. This interpretation can be accomplished by methods such as those used by Link (U.S. Pat. Nos. 3,903,872 and 4,154,238). Link et al (U.S. Pat. Nos. 4,009,709, 4,047,711, and 4,174,707), and Nunn (U.S. Pat. No. 4,427,013). In a preferred embodiment, during this phase, the amplitude data is correlated with standard patterns for systolic and diastolic pressures. The pressures corresponding to the peaks of these correlations are taken as systolic and diastolic pressures. These standard patterns have been derived from extensive measurements performed on human subjects. The systolic and diastolic presures derived from this analysis thus represent a "best match" of the amplitude data with the standard patterns.

Figure 4:
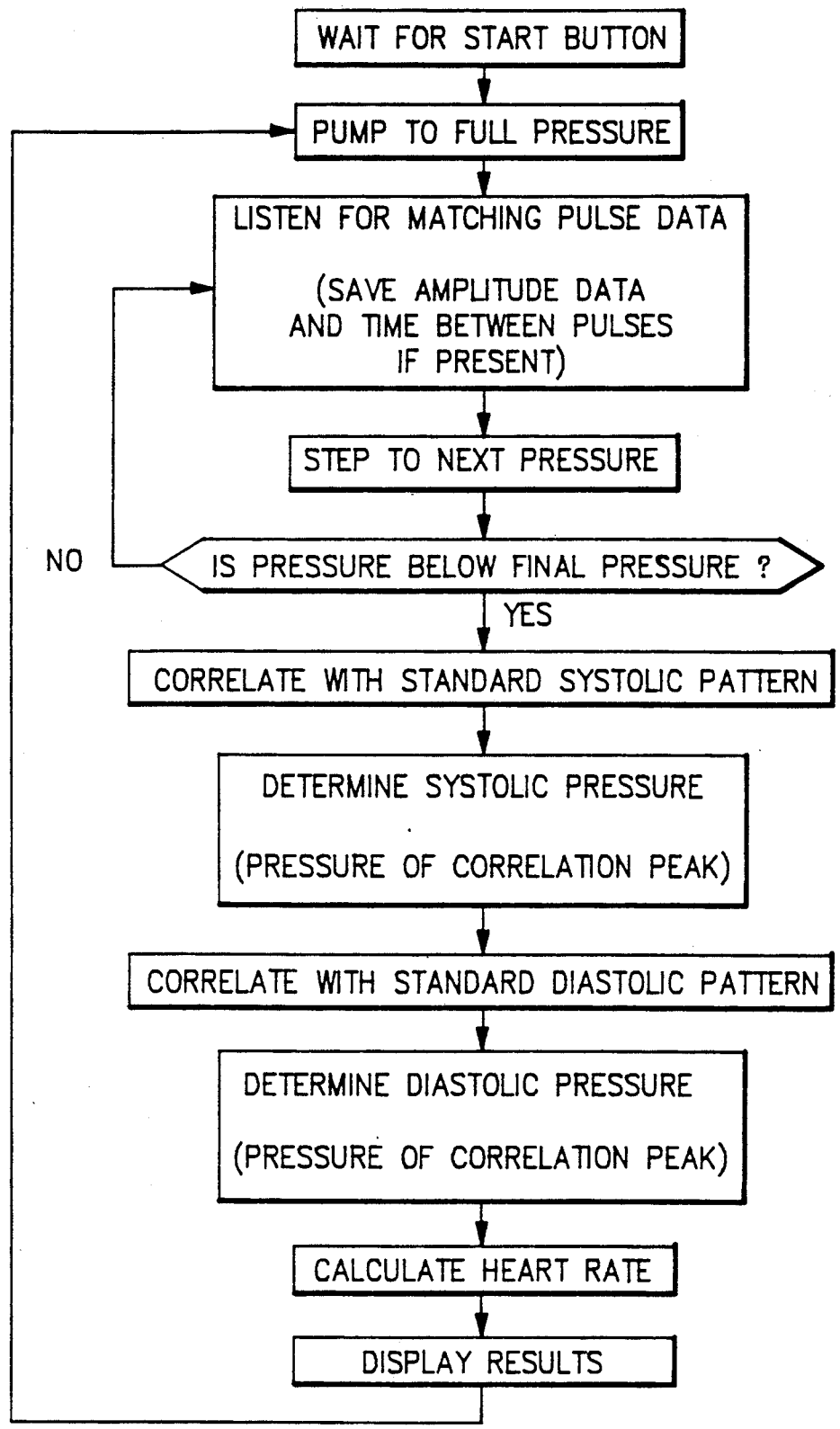
FIG. 4 shows an exemplary software routine flowchart for the system microprocessor.

FIG. 4 shows exemplory software routine flowcharts for the system microprocessor.

Hydrostatic pressure differences need to be accounted for in blood pressure measurement systems in order to obtain meaningful results. Hydrostatic pressure is simply the pressure of a fluid (such as blood or water) caused by the weight of that fluid. The weight of a fluid (blood in this case) will cause its pressure to be greatest at the bottom of its container and least at its top. In a standing person, for example, the blood pressure in the ankle can be 80 or 100 mmHg higher than in the upper arm just due to the weight of the blood. In fact, if a person's height is known, this pressure difference can be accurately predicted. Blood pressure at any point in a person's body is roughly 2 mmHg higher than at a point one inch above. This difference shows up in both the systolic diastolic pressures. The generally accepted meaning of blood pressure is that blood pressure as measured at the level of the heart. An upper arm measurement satisfies this requirement automatically. However, the results of a finger measurement will depend on the relative heights of the finger and heart. For this reason, and embodiment of the system according to the invention is a machine-mounted cuff system with measurements taken of the user in a seated position. This will bring the finger close to the heart level. Readings taken from the position of standing over such a machine-mounted cuff system will often be 2 to 30 mmHg higher than those taken while seated.

An alternate embodiment of the finger blood pressure measurement system according to the invention employs a remote finger cuff at the end of a short length of hose. This arrangement allows the machine itself to be located in a variety of places which would not be feasible with the machine-mounted cuff. It is important that the cuff be kept at heart level during use. The remote cuff allows users to be standing, sitting, or in any position as long as the cuff is brought to heart level. The machine can then be mounted on a wall, pedestal, or counter, as contrasted with a machine with a machine-mounted cuff which should be provided with a seat and table surface in order to bring the cuff to heart level for all users. A small flexible hose provides the air connection to the alternative embodiment machine's pneumatic system. This hose allows the cuff to be inflated and carries the pulse signals back to the machine. In addition, a stronger yet flexible hose is used as a protective jacket over the smaller air signal hose. This jacket prevents kinking of the inner hose and makes vandalism more difficult.

While the present invention has been described in connection with preferred embodiments thereof, it is to be understood that additional embodiments, modifications, and applications which will become obvious to those skilled in the art are included within the spirit and scope of the invention as set forth by the claims appended hereto.

We claim:

1. An oscillometric system for blood pressure measurement, comprising:
    aninflatable air pressure bladder disposed for occlusion of user finger arteries in an inflated state,
    a transducer means, coupled to said bladder, for measuring pulse and cuff pressure components of air pressure variations in said bladder.
    an air pressure reservoir, having a substantially larger air volume than said bladder in said inflated state.
    an air communication means, coupling said bladder to said reservoir, for allowing communication therebetween, including an isolating means located at a point between its ends for effectively isolating said pulse pressure components to the bladder side of said isolating means,
    a valve means, coupled to said reservoir, for bleeding down air pressure in said bladder and said reservoir,
    a pump means, coupled to said reservoir, for pumping up air pressure in said bladder and said reservoir,
    control means, coupled to said transducer means, said pump means and said valve means, for controlling operation thereof, and for deriving user blood pressure information, and display means, coupled to said control means, for displaying said user blood pressure information.

2. A system according to claim 1, further comprising:
a rigid cylindrical housing, wherein said bladder is mounted, for receiving a user finger for said measurement.

3. A system according to claim 1, wherein at least a portion of said air communication means is flexible so that said bladder may be adjustably located remotely from said reservoir.

4. A system according to claim 1 wherein said transducer means is coupled to said bladder via said air communication means at a point between said bladder and said isolating means.

5. An oscillometric system for blood pressure measurement, comprising:
an inflatable air pressure bladder disposed for occlusion of user finger arteries in an inflated state,
a transducer means, coupled to said bladder, for measuring pulse and cuff pressure components of air pressure variations in said bladder,
an air pressure reservoir, having a substantially larger air volume than said bladder in said inflated state,
a means for increasing the air pressure in said reservoir,
a means for decreasing the air pressure in said reservoir, and
an air communication means, coupling said bladder to said reservoir, for allowing communication therebetween, including a concentrating means, located at a point between its ends, for concentrating said pulse pressure components in said bladder.

6. A system according to claim 5, wherein:
said means for increasing the air pressure comprises a pump, and
said means for decreasing the air pressure comprises a valve.

7. A system according to claim 5, further comprising:
a microcomputer means, coupled to said means for increasing the air pressure said means for decreasing the air pressure and said transducer means, for controlling the operation thereof, and for deriving user blood pressure information.

8. A system according to claim 5, further comprising:
a rigid cylindrical housing wherein said bladder is mounted, for receiving a user finger for said measurement.

9. A system according to claim 5, wherein at least a portion of said air communication means is flexible so that said bladder may be adjustably located remotely from said reservoir.

10. A system according to claim 4 wherein said transducer means is coupled to said bladder via said air communication means at a point between said bladder and said concentrating means.

11. An oscillometric blood pressure measurement system, comprising:
a cuff;
an air storage means for slowing the rate of inflation and deflation of said cuff so as to gain more accurate control over air pressure variations in said cuff;
a means for increasing the air pressure in said air storage means;
a means for decreasing the air pressure in said air storage means;
a single pressure transducer means, connected to said cuff for measuring both pulse and cuff pressure components of air pressure variations in said cuff; and
an air flow restriction means connected between said air storage means and said cuff, for transmitting said cuff pressure components to and from said cuff, and for concentrating said pulse pressure components in said cuff.

12. A system according to claim 11, wherein:
said means for decreasing the air pressure comprises a valve, and
said means for increasing the air pressure comprises a pump.

13. A system according to claim 11, further comprising:
a microcomputer means, coupled to said means for increasing the air pressure, said means for decreasing the air pressure and said transducer means, for controlling the operation thereof, and for deriving user blood pressure information.

14. A method for measurement of blood pressure comprising the steps of:
placing an inflatable bladder around the limb of a subject,
controlling the inflation an deflation of said bladder through the use of a microcomputer connected to an air pump, an air storage means, and a valve,
restricting the flow of air to and from said bladder so that cuff pressure components of air pressure in said bladder are transmitted between said air storage means and said bladder, while pulse pressure components of air pressure in said bladder are concentrated in said bladder,
measuring said cuff and pulse pressure components of air pressure in said bladder, during said inflation and deflation, by the use of a transducer connected to said bladder and said microcomputer, and
peforming computation, with said microcomputer, on data obtained from said measurement of cuff and pulse pressure components so as to determine the systolic and diastolic pressure of said subject.

* * * * *